(12) United States Patent
Lundback et al.

(10) Patent No.: US 8,943,429 B2
(45) Date of Patent: Jan. 27, 2015

(54) STATE MACHINE USER AND VALIDATION INTERFACE SYSTEM

(75) Inventors: Stig Lundback, Vaxholm (SE); Jonas Johnson, Norrtalje (SE)

(73) Assignee: Gripping Heart AB, Huddinge (SE)

( * ) Notice: Subject to any disclaimer, the term of this patent is extended or adjusted under 35 U.S.C. 154(b) by 1274 days.

(21) Appl. No.: 12/746,066

(22) PCT Filed: Dec. 2, 2008

(86) PCT No.: PCT/SE2008/051393
§ 371 (c)(1),
(2), (4) Date: Jun. 3, 2010

(87) PCT Pub. No.: WO2009/072971
PCT Pub. Date: Jun. 11, 2009

(65) Prior Publication Data
US 2010/0281413 A1    Nov. 4, 2010

(30) Foreign Application Priority Data

Dec. 3, 2007    (SE) ........................................ 0702679

(51) Int. Cl.
*G06F 3/048*    (2013.01)
*G09B 23/28*    (2006.01)
*G06F 19/00*    (2011.01)

(52) U.S. Cl.
CPC ............ *G09B 23/288* (2013.01); *G06F 19/321* (2013.01); *G06F 19/3481* (2013.01); *G06F 19/3437* (2013.01)
USPC ............................. 715/771; 715/804; 715/810

(58) Field of Classification Search
CPC  G06F 19/3437; G06F 19/321; G06F 19/3481
USPC .......................................... 715/771, 804, 810
See application file for complete search history.

(56) References Cited

U.S. PATENT DOCUMENTS

| 5,103,819 A | 4/1992 | Baker et al. |
| 5,431,691 A | 7/1995 | Snell et al. |

(Continued)

FOREIGN PATENT DOCUMENTS

| WO | 01/88642 A1 | 11/2001 |
| WO | 02/32035 A2 | 4/2002 |

(Continued)

OTHER PUBLICATIONS

International Search Report, dated Mar. 4, 2009, from corresponding PCT application.

(Continued)

*Primary Examiner* — David Phantana Angkool
(74) *Attorney, Agent, or Firm* — Young & Thompson

(57) ABSTRACT

State machine interface system, comprising state machine algorithms and a graphical user interface, adapted to receive signals from at least one sensor device, that are related to physiological activities of the heart and/or the circulatory system of a living being. The state machine algorithms are adapted to determine phases of heart cycles based upon said signals. The different phases of the heart cycle are determined by said state machine algorithms in a heart cluster state machine simulating the heart, and optionally the circulatory system, achieved by fusions of finite heart muscle cell state machines to form a ΔV-pump state machine. The determined heart cycle phases are evaluated by determining their respective local state diagram based upon said signal such that the respective correct time duration is determined for each heart cycle phase, and then determining the most representative global state diagram. The determined local and global state diagrams are presented at the graphical user interface such that the temporal relations between the different phases are illustrated.

20 Claims, 15 Drawing Sheets

(56) References Cited

U.S. PATENT DOCUMENTS

| | | | |
|---|---|---|---|
| 5,692,907 | A | 12/1997 | Glassel et al. |
| 5,947,899 | A | 9/1999 | Winslow et al. |
| 6,366,810 | B1 | 4/2002 | Johnson et al. |
| 7,346,381 | B2 * | 3/2008 | Okerlund et al. ............ 600/407 |
| 8,379,955 | B2 * | 2/2013 | McKenzie et al. ............ 382/131 |
| 8,560,057 | B2 * | 10/2013 | Lundback .................... 600/513 |
| 8,566,115 | B2 * | 10/2013 | Moore .............................. 705/2 |
| 8,617,075 | B2 * | 12/2013 | Tsujita et al. ................ 600/443 |
| 8,666,482 | B2 * | 3/2014 | Wegerif ........................ 600/515 |
| 8,672,884 | B2 * | 3/2014 | Burnett et al. ............... 604/113 |
| 2006/0030902 | A1 | 2/2006 | Quiles |
| 2009/0005679 | A1 * | 1/2009 | Dala-Krishna ............... 600/437 |
| 2010/0281413 | A1 * | 11/2010 | Lundback et al. ............ 715/771 |
| 2012/0277786 | A1 * | 11/2012 | Mohl ............................ 606/194 |
| 2013/0226011 | A1 * | 8/2013 | Zhang et al. ................. 600/484 |
| 2014/0125691 | A1 * | 5/2014 | Lysyansky ................... 345/619 |
| 2014/0135878 | A1 * | 5/2014 | Burnett et al. ............... 607/105 |

FOREIGN PATENT DOCUMENTS

| | | |
|---|---|---|
| WO | 2004/084088 A1 | 9/2004 |
| WO | 2006/079042 A2 | 7/2006 |
| WO | 2006/080887 A1 | 8/2006 |
| WO | 2007/142594 A1 | 12/2007 |
| WO | 2008/013497 A1 | 1/2008 |

OTHER PUBLICATIONS

Lewan, Mats: "Gripping Heart :Med full koll pa pumpen", May 26, 2005, Retrieved from the Internet; www.Nyteknik.se.

Lewan, Mats: "Gripping Heart: With full control of the pump Technology in Growth", May 26, 2005, Swedish to English Google Translation.

International Search Report in Corresponding Application No. PCT/SE2008/051393 dated Mar. 4, 2009.

* cited by examiner

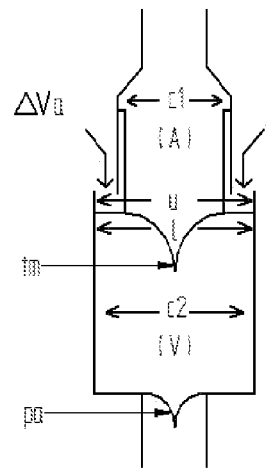
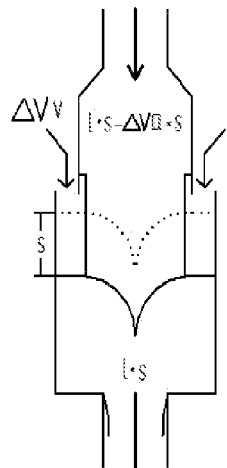
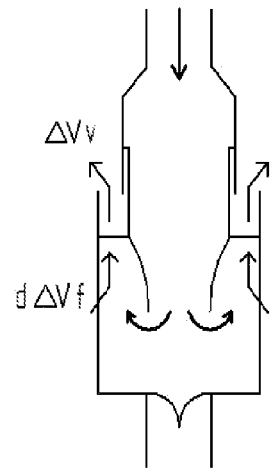
Fig. 1a    Fig. 1b    Fig. 1c
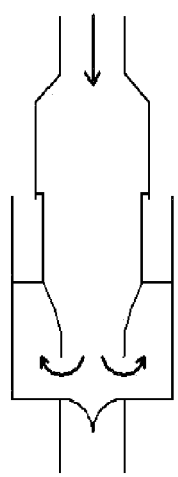
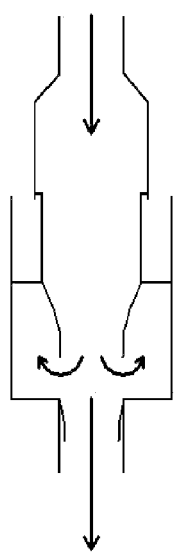
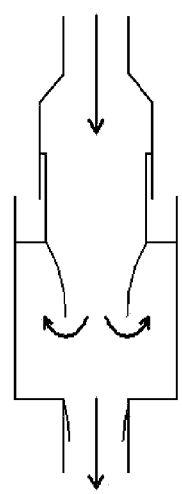
Fig. 1d    Fig. 1e    Fig. 1f Frontal MRI picture Frontal MRI picture

Global State Diagram with stroke lengths

| | Old names / color | | New names / color |
|---|---|---|---|
| | Volume to Tension | | Pre-Ejection |
| | Ventricular Ejection | | Ventricular Ejection |
| | Tension to Volume | | Post-Ejection |
| | Fast DeltaV | | Rapid Filling |
| | Slow DeltaV | | Slow Filling |
| | Atrial Contraction | | Atrial Contraction |

STATE MACHINE USER AND VALIDATION INTERFACE SYSTEM

FIELD OF THE INVENTION

The present invention relates to a state machine interface system according to the preamble of the independent claim.

BACKGROUND OF THE INVENTION

The present application is related to the following international patent applications: WO-2006/080887, PCT/SE2007/050366 and PCT/SE2007/050511 by the same assignee as in this application.

In order to fully understand all aspects of the present invention an accurate description of the background to the invention will be given in the following.

The pumping function of the heart has been differently described during the years. The discussion is mainly focused on if the heart pumps with squeezing motions or if it works as a pressure suction pump. As a result of a theory presented in 1986 regarding the heart's pumping and regulating function a new class of pumps has emerged, so called dynamic displacement pumps ($\Delta$V-pumps). It has been proven that pumps within this technology have the same characteristics as the natural heart such as being controlled by inflow, no increasing static filling pressures at high rate and flow, closing valves with no backflow and ability to create a continues inflow though a pulsating outflow. According to this theory, it is mainly the longitudinal motion of the spherical AV-piston ($\Delta$V-piston) that contributes to the heart's pumping function. As described in detail in the above-mentioned international patent applications the heart is a cluster-state machine of heart-muscle state machines and $\Delta$V-pump state machines working according to their internal and external boundary conditions.

The heart cycle can be divided into six main phases creating six transitional zones that will be influenced by the boundary conditions of the heart being that mentioned cluster-state machine. The transitional zones between the phases are, from a mechanical point of view, the most interesting time intervals since their information are more or less a product of what happened in previous phases. Dividing the heart's functions into six main phases and knowing their boundary conditions for optimal functions makes it easier to see and understand when, where, why and how the heart changes its functions.

The Technology of the Pumping and Inflow Regulating Functions of the $\Delta$V-Pumps.

One of the key-functions of the DeltaV-pumps is their $\Delta$V-functions that can be divided into direct and indirect DeltaV-functions. The direct DeltaV-functions can generate, store and absorb energies into, inside and outside of the heart and transform these energies to a hydraulic return of the $\Delta$V-piston towards the base (the top) of the heart during diastole. The indirect DeltaV-functions create circumstances the can bridge the heart from one phase to another, that under normal conditions makes the heart to pump and regulate in very dynamic ways. The mechanics behind the DeltaV-pump and additional properties that optimize its functions under various conditions will stepwise be transformed to the heart's functions that may be considered to be the most sophisticated DeltaV-pump. The first step with its limitations is explained by a schematic stiff model of a DeltaV-pump. The second step with fewer limitations is described and animated by a man-made flexible DeltaV-pump. The third step adapting all the other good feasibilities and further reducing the limitations with additional regulating functions will be described by an authentic model of the heart. Finally, and which in particular being an issue of the present invention, authentic values obtained by Tissue Velocity Imaging (TVI) from well-trained, normal, ischemic and dyssynchronic subjects will be presented as novel state-diagrams and trend-curve formations reflecting cam-curve formations that are generated by heart-muscles.

The DeltaV-Pump Described as a Stiff Schematic Model

The DeltaV-pump is a piston pump. The design of the piston makes the pump to be a DeltaV-pump. The piston of mechanical DeltaV-pumps will from now on be expressed as the DeltaV-piston and in relations to the heart it will be expressed as the AV-piston. The general piston design can be described as follows with references to FIGS. 1a-1f. The DeltaV-piston has an upper area (u) and lower area (l) that includes common valve-areas that with one or more check-valves (tm) that together with two cylinders (c1<c2) divide an internal enclosed volume into an inlet and outlet compartment (A) and (V). The upper area (u) is also, in its periphery in direct contact to the external volumes of the pump. This area is expressed as the direct DeltaV area ($\Delta$Va) of the pump. The theoretical model has constant cylinder diameters and piston areas. The driving means for the piston is not shown. Linear motions of the piston will thus produce linear volume-changes into, inside and out of the pump but also through the peripheral DeltaV-area external volume changes that will be expressed as direct DeltaV-volumes ($\Delta$Vv). The reasons for that expression will become clear later. During a displacement with a stroke-length of (s) the inflow to the pump will be (l*s−$\Delta$Va*s) and the outflow through the outlet valves (pa) will be (l*s) since the upper (u) and lower (l) areas are equal (see FIG. 1b).

The Direct DeltaV-Functions

The DeltaV-piston generates through the direct DeltaV-areas direct DeltaV-volumes during the displacement phase that can be refilled during its reverse motions. The refilling process (see FIG. 1c) generating the piston return and the inflow controlled auto regulating function is referred to as the direct DeltaV-functions marked as d$\Delta$Vf in FIG. 1c. The piston return can either be done by e.g. external resilient forces generated by the motions of the DeltaV-areas and/or by dynamic and static forces generated by the whole area of the DeltaV-piston during the displacement phase. In the former case the resilient forces have to transform energy both to the piston return and to a continue inflow to the pump. In the later case de dynamic and static forces of the flow into and inside the pump will transform energy to the piston return and motion of masses associated to the DeltaV-areas. It is obvious that if the flow into the pump is low compared to the direct DeltaV-volumes to be refilled, the returning speed of the DeltaV-piston will be low. This makes the auto regulating functions of the DeltaV-pumps.

Asymmetric Time-Shifts Work in Favour for the Dynamic Properties of the DeltaV-Pump.

A good working pump should have as smooth and constant inflow as possible. Theoretically, a DeltaV-volume, having 50% of its stroke-volume as direct DeltaV-volumes, would be suitable to generate a constant inflow to the pump. However, it is impossible to generate instant reciprocating motions, accelerations and decelerations (see FIG. 1d). This problem can be dealt with by adding more time to the displacement period of the pump-cycle and consequently reduce the time for the hydraulic return of the piston. Now the DeltaV-volume has to be reduced in relation to the differences in time between the displacement and returning period of the piston in order to be able to create a continuous inflow. The time that has to be added to the displacement period is depending on the pistons acceleration and deceleration periods. A prolonged displacement period has another good feature, it prolongs the time for accelerations of the masses into, inside and out of the pump.

Venturi Effects Facilitate the Dynamic Properties of the Pump.

The flow into and out of the pump will be disturbed and reduced if the valves (tm) and (pa) are closed by backflow. This can in the schematic stiff model be avoided by keeping up the kinetic energies into, inside and out of the pump as close to the end of the displacement phase as possible. That will, as in the garden-pump, generate venturi effects that can keep up the flow into, inside and out of the pump during the power-reduction and mechanical relief of the driving forces from the piston. At the end of the displacement phase the inflow to the pump has two ways to go. One way is to follow the venturi effects out of the pump. The other way is to refill the direct DeltaV-volumes by forcing the DeltaV-piston back.

Since the pressure out of the pump is higher than the pressure into the pump, the flow out of the pump will decrease much faster than the flow into the pump. The difference in flow into and out of the pump can be used to bring the piston back (see FIGS. 1e and 1f).

A Cam-Curve Formation is a Practical Mechanical Solution to Optimize the Dynamic Properties of the Pump.

Mechanically a suitable cam-curve formation with a longer progressive displacement phase and a steep re-entry phase can be made to both transform power to the DeltaV-piston during the displacement phase and disconnect the piston from power during its hydraulic return. The cam-curve formation can be optimized to keep up the flow and kinetic energy into, inside and out of the pump to the end of the displacement phase generating the best possible venturi effects that the actual power-source can generate. At high flow and frequencies with asymmetric driving-sources, and well-balanced direct DeltaV-volumes, the outflow valve (pa) does not need to be closed before the next displacement phase is about to take place. The inlet valves (tm) will also in this case be closed by catching up the flow through the pump.

Limitations of a Stiff DeltaV-Pump Construction

At low flow and frequencies both the inlet and outlet valves will be closed by backflow. A small motion of the large DeltaV-piston area at the beginning of the displacement phase will generate a backflow over the inlet valve that not can be compensated for by the same motion of the small valve area. This will disturb the inflow to the pump. A fast acceleration during the displacement phase might occlude the inlet tubing. The closing of the outflow valve will create a backflow that will force the piston to return before the inlet valve is opened. That will seriously disturb the filling and hydraulic return of the DeltaV-piston. This means that the transitional phases of the piston-motions have to be compensated by other arrangements, indirect DeltaV-functions, to keep up the dynamic properties of the DeltaV-pump especially at low flow and frequencies.

Flexible DeltaV-Pump Constructions can Generate Indirect DeltaV-Functions as Indirect DeltaV-Volumes, Flexible Power Transmissions and Counteracting Resilient Suspensions.

Flexible DeltaV-pump constructions can by the motions of the DeltaV-piston through indirect DeltaV-areas generate indirect DeltaV-volumes associated to the inflow compartment of the pump or the atria compartments of the heart. It can also generate a flexible power-transmission as in the muscles of the heart. It cannot, due to pushing driving forces, as easy as the heart, create a resilient suspension of the ventricular volumes that improves the filling to the heart by creating relative motions of the ventricle volumes and counteracting motions to the piston. Instead the flexible power transmission has been enhanced to match that function.

Indirect DeltaV-Functions and the Volume to Tension Phase and the Tension to Volume Phase.

The flexible DeltaV-pump constructions have except the direct DeltaV-functions asymmetric time-shifts and the described venturi effects also other unique possibilities to produce continuous inflow at any flow and frequencies. In order to achieve these features the DeltaV-pumps, as the heart, have to be made of cylinders and DeltaV-pistons that in total or partly are made of flexible materials imbedded in flexible surroundings. These constructions produce besides the direct DeltaV-volumes also external volume changes related to the inflow compartments of the pump and in case of the heart, through its resilient suspension later described, also external volume changes related to its outflow compartments. These volume changes that are generated and have impacts on the reciprocating motions of the DeltaV-piston are referred to as indirect DeltaV-volumes and indirect DeltaV-functions. They can, by storing and releasing energies and volumes, smoothen and keep up the flow into the pump during the two transitional phases of the DeltaV-piston motions referred to as the volume to tension phase and tension to volume phase.

FIG. 2 illustrates a man-made flexible DeltaV-pump has two flexible bulbs (A) and (V) that can serve as the inlet and outlet compartments of the pump. The bulbs are joined to each other through a valve (tm) that serves as the inlet valve to the outlet-compartment (V) that also is equipped with an outlet valve (ap). Between the two bulbs a light-weighted pusher-plate (P) is fixated to the inlet valve (tm) to be able to transfer energy to the inlet bulb (A) by suction and outlet bulb (V) by compression. The pusher-plate has a spherical surface area that during compressions of the outlet bulb creates a roller-membrane function. The inlet bulb will during the same motions of the pusher-plate be decompressed by a spherical area belonging to the housing (H) that surrounds the pump. The rods (R) are by single acting forces transforming energy to the pusher-plate that at the sometime both compresses the outlet bulb and decompresses the inlet bulb. This will create an upper (U) and lower spherical piston area (L) that varies in sizes and two cylinder-functions that varies in diameters. The differences between these two areas (L)-(U) will be the direct DeltaV-aria that by motion creates the direct DeltaV-volumes as earlier described in the example of schematic DeltaV-pump fig. (x). Since the pump is encapsulated in a sealed casing filled with an air volume the DeltaV-areas will by motions of the piston create pressure changes within this air-filled volume. During the displacement phase more fluids will leave the pump than entering into it. The difference is not only generated by the production of direct DeltaV-volumes but also through a production of indirect DeltaV-volumes associated to external volume changes of the whole inlet bulb or the atria of the heart. The volume differences will result in a decompression of air inside the casing if the Pressure Control Valve (PCV) is closed. The decompression of air will act like stored resilient forces.

The compression and displacement of fluid out of the outlet bulb will at the sometime also generate a longitude expansion and volume increase of the inlet bulb. That volume expansion can either be filled by increasing inflow to the pump and or be compressed due to that the suction forces that are needed to increase the flow into the pump are larger than the decompressing forces outside the inlet bulb. Compressing the inlet bulb will further together with continuous production of the direct DeltaV-volumes increase the decompression of air inside the casing. That will continue until the decompressing forces are in balance with the forces that are needed to increase the inflow to the heart. Once the fluid into the pump has been accelerated and excides the longitude volume expansion of the inlet bulb done by the DeltaV-piston the decompressing or resilient forces behind the indirect DeltaV-volumes can release energy and continue to fill the inlet bulb by radial expansions. These external volume changes absorbing and releasing energies are useful to smooth the flow into the pump especially during its transitional phases and are referred to as indirect DeltaV-functions. Other mechanical arrangements that can absorb and release energies to smooth the inflow and bridge the time of slow and no velocities of the piston at the end of the displacement phase are done by flexible power transmissions and resilient suspensions of the ventricular volumes. The last arrangement can only be demonstrated by analyzing the heart as a flexible DeltaV-pump.

Flexible Power Transmission.

A flexible power transmission, being a part of the indirect DeltaV-functions, can be used to absorb and release energy at the end of the displacement phase to keep up the flow into, inside and out of the pump and thus support the venturi effects at the end of the displacement phase. In the man-made flexible DeltaV-pump that energy is stored as elastic recoiling forces in the walls of the poly-urethane outlet bellow that are stretched out in the areas creating the Direct DeltaV-volumes. That stored energy can be released when the pressure inside that bellow starts to decrease. This will directly support the outflow of the pump but also indirectly through the decompressed air around the bellow support the inflow to the pump. In this way it will have similar effects as the resilient suspension of the heart, later being described. That will keep up the kinetic energy both into and out of the pump though the true motion of the DeltaV-piston is slowing down at its transitional zone. This will together with the flow-characteristics of the outflow tubing's work in favour for venturi effects and brings the pump in a good dynamic mood. At low flow and frequencies the rest of the stored resilient forces in the flexible power transmission can after a mechanical release of the power-source support a rapid return of the piston to generate a volume expansion that take care of the both the backflow closing the outlet valve and volumes that opens the inlet valves.

All forces that are involved with accelerations, motions and pressures of fluid into and inside and out of the pump including all recoiling forces are balanced between the pusher-plate and the rigid casing covering the pump. The flexible polyurethane bellows makes the pump to have a flexible power transmission. The heart made and driven by muscle cells has its flexible power-transmission within the heart-muscle constructions, and also as a resilient suspension to the apical-diaphragm areas of the heart.

The Resilient Suspension.

Instead of rigid casings a resilient suspensions outside the pump can be used to generate, accumulate and release counter-acting forces to the motions of the piston. This is another way to store energy to improve and smoothen, especially the inflow to the pump once the DeltaV-piston stops its motions at the end of the displacement phase and at the beginning of its returning phase. The resilient suspension is thus another mechanical function within the indirect DeltaV-functions. This special function is hard to accomplish and demonstrate by a man-made device but is easily found and demonstrated by looking at the motions of the natural heart.

The limitations of the flexible DeltaV-construction compared to the heart are mainly its driving line and external driving force. It cannot, as the heart, produce a "gear down effect" further being described below.

A Theoretical Model of the Heart

In order to understand the similarities between the heart and the man-made flexible DeltaV-pump, a brief summary of the differences in constructions have to be addressed. The heart's function will also be set in relations to the major phases that the heart is passing during a heart-cycle. Finally authentic TVI (tissue velocity imaging) values from well-trained, normal, ischemic and dyssynchronic subjects are presented as novel state-diagrams and trend- or cam-curve reflecting formations.

The Outflow Tracts being Parts of the Direct DeltaV-Volumes.

The heart can be considered as a fusion of two DeltaV-pumps having a common AV-piston with inlet and outlet compartments formed by the outer contours of the right and left atria and ventricles schematically shown in FIGS. 3a-3d. These two pumps are encapsulated in a flexible but not very stretchable pericardial sack.

All the above described DeltaV-pumps have been described with only the inlet valves being a part of the DeltaV-piston. The heart also has its outflow valves and outflow vessels T. Pulmonalis and the Aorta connected to the piston area. In FIG. 4 it can be seen that the right ventricle is attached to the strong muscles of IVS being a part of the left ventricle. This will make the right side to have a lunar shaped form in a cross-sectional view in the plane of its short axis. In this way IVS will serve as a power source both for the left and right ventricular motions of the common AV-piston. It can be understood that motions of the outflow areas (see FIGS. 5 and 6) during the displacement phase as the rest of the piston areas contribute to the stroke-volumes out of the heart. The inflow patterns to the ventricles to replace the volumes that these areas generate during the reverse motions are quite complex but very suitable for the heart being a DeltaV-pump. The outflow areas of the AV-piston are above the outlet valves due to their connections to the outflow vessels in no direct contact to the inflow compartments. The outflow vessels are attached to the AV-piston at specific angles. Their motions above the piston but inside the pericardial sack, are to some parts covered by the auricles of the atria (see FIG. 6) and their appendices, and will in this way generate indirect contacts to the inlet volumes of the heart. During the return of the AV-piston these outflow areas, besides redistribution of volumes between the atria and ventricles, also as the rest of the direct DeltaV-volumes, need external inflow to the heart to be refilled. In this way the outflow areas will be a part of the direct DeltaV-areas and be a part of the direct DeltaV-functions creating a hydraulic return of the AV-piston.

At low flow and frequencies, and low or no venturi effects, the closing of the valves in T. Pulmonalis and Aorta will be done by backflow. That backflow is a result of lower static pressures in the ventricles than inside the vessels. This means that the heart-muscles no longer have power enough to generate force vectors that can withstand the pressures that are generated by the backflow. The backflow results especially on the left side of the heart having a higher diastolic pressure in a short expansion and returning motion of the left ventricular part of the AV-piston. Once the outflow valves are closed the expansion forces are reduced. Other forces described below will now take part in returning the AV-piston making the heart ready for a new pump-cycle.

The Regulating Functions of Inter Ventricular Septum (IVS)

The right and left side of the heart generate a common AV-piston. It has a common central flat area, the ring of annulus fibrosis that contains all four valves. The spherical parts of the pistons are made by the heart-muscles. The spherical areas of the common AV piston are to quite large extent covered by the auricles and their appendices belonging to the atria volumes and the expandable and deformable fat-keel (wedge) seen in the schematic FIG. 3a. IVS can be seen as a part of the left ventricle and has, except for the outflow tract of the aorta, a spherical connection to the mitral ring the inflow valve to the left ventricle. The spherical connection will thus be a part of the left ventricular AV-piston that through its attachment to the common AV-piston supports the right ventricle piston with motions and will also generate internal DeltaV-volumes belonging to the left ventricle (see FIG. 3d). IVS also serves as a balancing force to the pressure gradients that are generated between the two ventricles.

IVS will during its relaxed phase serve as a mediator of pressure and flow into all compartments of the heart resulting in that the heart during this time-period will act as if it was a common large DeltaV-pump controlled by inflow. In the beginning of its contraction phase its motions together with its other functions will transform volumes between the ventricles to maintain proper flow and pressures over the pulmonary and main circulatory system.

IVS will also together with the rest of the ventricular muscles contribute to bend and untwist T. Pulmonalis and the Aorta that can be one of the reasons for the rotating motions of the heart.

The Counteracting Resilient Suspension.

The heart does not have a rigid casing, supporting the pushing and compressing forces done by the pusher-plate. Instead the heart is driven by pulling forces that have a base, the upper part of the heart, that quite strongly, via the pericardial sack and the inflow-vessels, is fixated by connective tissues to the surroundings and makes the base resistant to motions. The hearts apical-diaphragm area is approximately to one half generated by the right ventricle and to the other half by the left ventricle. This area has through the pericardial sack a tendon-like fixation to the flexible and movable diaphragm. The heart is further, through large surface areas of the right ventricle including its outflow tract and some areas of the anterior and apical part of the left ventricle, through the pericardial sack, in a close but not fixated contact to sternum. This close contact will serve as a hydraulic attachment of the heart to sternum, allowing it to slide and rotate in parallel with sternum but not leaving it. That is a very suitable construction since the diaphragm is moving several centimeters during the breathing cycle. As seen in the MRI pictures (see FIGS. 5 and 6) a pulling of the AV-piston by right and left ventricular contractions will generate tension forces in the outflow vessels that can be matched by counteracting forces generated by a lifting and stretching of the diaphragm area. The lifting of the diaphragm area will be shorter at the apical area than at the regions closer to atria areas since the distance to the diaphragm's own spherical fixation to sternum is short at the apical area of the heart. This will result in a slight tilting of the left ventricle into the right ventricle during ventricular systole. It can also be seen in FIG. 7 that tensions of T. Pulmonalis generate tension forces that by mechanical forces will twist the heart around the aortic root. Other forces generated above the AV-pistons like the resilient forces in the surroundings of direct and indirect DeltaV-volumes and the atria and their auricles being stretched and filled with blood, also need counteracting forces. These forces can be generated and absorbed by the heart's fixation to the diaphragm area. It is to be noticed that the tension forces inside the ventricles and their muscles during ventricular systole do not need any external counteracting forces, though these forces are balanced by the pressures that are generated inside the ventricles.

The resilient suspension will reduce the systolic stroke-length of the AV-piston in the regions causing these lifting functions. These regions are especially located to the outflow tracts of T. Pulmonalis and the Aorta and their connections to IVS and the AV-piston. The reduced motions of the AV-piston do not reduce the total stroke volumes out of the pump since they are compensated by the volume shift that appears when the left ventricle is tilted into the right ventricle (see FIG. 3d). This will increase the stroke-volume out of the right ventricle, but that will be compensated by the spherical connection of IVS towards the DeltaV-piston generating internal DeltaV-volumes belonging to the left ventricle (see FIG. 3d).

The Resilient Suspension is in Balance with the Upper Resilient Forces.

The resilient suspension absorbs during the systolic phase energy that partly can be stored and released as resilient forces. When the motions of the right and left AV-pistons start to decline and the static and dynamic forces of the inflows exceed the volume expansions, that the moving AV-piston can generate, the indirect DeltaV-volumes can start to release their stored energy and be refilled. This will reduce the resilient forces behind those volumes. The inflow will also reduce, or even at high flow reverse, the forces that are acting on the upper areas of the still pressurized DeltaV-piston. This results in that the resilient suspension will start to pull the still contracted ventricles including the DeltaV-piston a little bit further and thus expand the inlet compartments. In this way the resilient suspension in balance with the resilient forces above the AV-piston, can keep up and improve the dynamic properties of the inflow when the true motions of the right and left side of the common AV-piston is zero or close to zero.

This can continue until the ventricular relaxation process starts and the DeltaV-functions and other separating forces and volume consummating processed start. This is a critical feature to the right side of the heart since it is working with very low static filling pressures which mean that there are not much stored energy that can compensate disturbances of the dynamic forces which immediately will have impacts on the hearts filling.

The Ventricular Relaxation Process, the Tension to Volume Phase and the Rapid DeltaV-Function Phase The relaxation or release of contraction forces of a heart-muscle cell is, apart from time, also dependent upon elongating forces. Stronger separation forces of the ventricles will at the time of relaxation speed up the relaxation process. Once the contraction forces, including the tension forces, inside the muscles become lower than the sum of the two counteracting forces that want to separate the AV-piston from the Apex, a true relaxation and elongation of the muscle-cells will occur. The two counteracting forces may be denoted as upper and lower resilient forces and separation forces made by the direct DeltaV-functions. The upper resilient forces consist of the resilient forces behind the direct and indirect DeltaV-volumes and other resilient forces related to the atria and the outflow vessels. The lower forces are related to the resilient suspension and other resilient forces related to the conical ventricular part of the heart. The dynamic and static forces powering the direct DeltaV-functions will contribute to the separating process in different ways depending on stored energies and the heart's dynamic properties. At low flows into the heart and low or no venturi effects, with no time within the displacement phase to release the tensions in the ventricular muscles, this time will be transferred to the relaxation process. The dynamic energy powering the DeltaV-functions and the separation process of the ventricles will be reduced. In this situation the other separating forces transforming tension to volumes will be more dominating and add energies to the flow into and inside the heart, expand the ventricles, and force the piston back. The relaxation process referred to as the tension to volume phase, will in this way by flow-dynamic reasons be prolonged. At high flows and frequencies the venturi effects out of the heart will render in more dynamic inflows and more time and forces to release the tensions in the muscles during the displacement phase and generate strong forces behind the DeltaV-functions with strong separating forces and a rapid and forceful DeltaV-function. This phase is referred to as the rapid DeltaV-function phase.

The Slow DeltaV-Function Phase.

The heart has an egg-like shape with the largest diameter where the spherical AV-piston is attached to the more conical part of the heart. The spherical AV-piston has quite large areas covered with volumes and masses that can be pressurized with fairly the same static filling pressures both above and below the AV-piston and thus create no net-forces that can move the piston. The non-covered areas of the spherical AV-piston, the direct DeltaV-areas, will, as the rest of all outer contours of the heart at static filling conditions, be pressurized with fairly equal static pressures. This will create a widening of the heart's egg-shaped form being narrower at the end of the rapid DeltaV-function phase as a consequence of low inflow and the compensatory mechanism now being described. During the widening of the heart the AV-piston will also become wider but not necessarily increase its distance to the Apex of the heart. Its motions during this phase referred to as the slow DeltaV-function phase is in balance with the forces acting on its upper and lower areas. The inflow and widening of the heart can continue until the widening is restricted by the flexible but not very stretchable pericardial sack. As in the man-made pump there is a feed-back system, the Bainbridge reflex that increases or decreases the frequencies of the heart depending on e.g. the central venous pressures. The slow DeltaV-function phase delays the starting point of the next phase that in the natural heart is the atria contraction phase. This phase and the atria contraction phase result in that the area and the stroke-length of the piston will be optimized to inflow and stroke-volumes that are well-adapted to the muscle forces and the displacement velocities. That will secure a flow out of the heart that can create venturi effects and dynamic conditions that even at low flows and frequencies can make use of the tension forces within the ventricular muscles during the displacement phase and make the tension to volume phase to be as short as possible. The separation forces will be reduced due to a low inflow during the displacement phase that will be compensated with an increase of the indirect DeltaV-volumes around the atria volumes in connections to the direct DeltaV-volumes. The refilling of the indirect DeltaV-volumes creates low static pressures either by a continuous retransferring of energy to the flow into the heart as describe above or consuming inflow by being refilled. This reduces the power behind the separating forces and can prolong the tension to volume phase if the tensions forces within the heart-muscles are not reduced below the separation forces exerted by the counteracting resilient forces. Once this occurs, these forces in the beginning of the rapid DeltaV-function phase can force the AV-piston and the Apical-diaphragm region apart and add energy to the flow into and inside the heart that together with rest of the resilient forces make a continuous return of the piston into more narrow egg-shaped form of the heart. A new slow DeltaV-phase can start and wait until the heart has expanded enough by being refilled. Once that is done the Bainbridge reflex can initiate a new heart-cycle. This makes the heart very sensitive to inflow.

Atria Contraction Phase

Once the heart and the AV-piston have reached their largest sizes and neutral position inside a distended pericardial sack the only volume increase into the heart can be made by motions of the hearts outflow tracts and their connected vessels. This will increase the stroke length of the AV-piston at the area where IVS is fixated. This can be documented at high flow and frequencies when power behind the DeltaV-functions is high. Unlike the man-made flexible DeltaV-pump that can compress the whole inflow compartment with use of the deltaV-functions even by just static forces, the heart has chosen to add forces to increase the stroke-length at especially low flow and frequencies. This solution is also sometimes lifesaving during mal-functions of the heart.

During the atria contraction phase there will be a withdrawal of the masses and volumes covering the spherical part of the AV-piston. The withdrawal of these structures creates sliding forces and hydraulic attachments to the pericardial sack and the AV-piston that results in a lifting of especially the peripheral muscular part of the AV-piston. This results in rearrangements of blood above and below the piston and some tension forces within the ventricular walls and the resilient suspension. In this way the atria contractions, as a booster mechanism, will increase the stroke-length and make the pump more volume-effective when the dynamic forces into and inside the pump are low.

At high flows and frequencies the tension to volume phase will be very short and even disappear being a part of the rapid DeltaV-function phase. The dynamic forces will now be strong enough to force the piston above its neutral position and make the atria contraction to merge with the rapid DeltaV-function phase. They will further have impacts in shortening the volume to tension phase by closing the inlet-valves. In this way the forces generated by the atria contractions to elevate the AV-piston will be reduced which will further increase the stoke-length.

At high flows and frequencies the stored kinetic energies in the flow into, inside and out of the heart is much higher than the stored energies in the resilient forces inside and outside the heart. This means that the venturi effects will work with maximum forces, make use of all tension forces within the heart muscles and create large Ejection Fractions (EF). The inflow to the heart will fill out the indirect DeltaV-volumes and together with the venturi effect reduce the pressure gradients over the inlet valves at the end of the displacement phase and contribute to a large ejection fraction. The heart has, at high flow and frequencies, in principle, just its displacement phase and its rapid DeltaV-function phase left.

The heart will, as the man-made flexible DeltaV-pump, all the time, by its mechanical constructions, adapt its stroke-volumes and frequencies to the inflow as long as the power-supply behind the driving systems is equal to or below its maximum static and dynamic work-loads. With a reduced power-supply a reduction in static workload can serve as a compensating factor for an adequate pumping performance The Gear Down Effect of the AV-Piston.

The fact that the piston is flexible, made and driven by muscle-cells inside a flexible but not distensible pericardial sack, makes the piston to inherit another feature that is useful to make a smooth start and when the ventricular muscles become weak and/or have impaired contractions. This feature is referred to as the gear down effect of the AV-piston.

The spherical piston-area of the man-made DeltaV-piston increases its area towards the outlet bulb and decreases its area to the inlet bulb during the displacement phases. That may, from a construction point of view, be dealt with by adjusting the cam-curve formation and make the inlet bulb to be both flexible and distensible in order to absorb and release dynamic energies during the end of the displacement phase and beginning of the returning phase of the piston. However, the heart has a flexible spherical piston being pulled, that in principle works the other way around. It decreases its areas towards the ventricles and thus also decreases the largest diameter of the heart by generating direct DeltaV-volumes. These volumes are partly added to the indirect DeltaV-volumes that also are generated. This makes the heart to have a more narrow egg-shaped form during the displacement phase. The AV-piston area towards the atria and their auricle volumes will increase due to their hydraulic coupling to the spherical AV-piston and suctions forces generated by the direct DeltaV-volumes. The reduction of the areas towards the ventricles suits the characteristic force-release curve of a heart-muscle cells since they exerts their maximum power close to the beginning of the contraction with a continuous weakening during the rest of the contraction. The decreasing AV-piston area towards the ventricles reduces the forces needed to withstand the static pressures that are generated. Instead this release of forces can be used to keep up the kinetic energy into, inside and out of the heart at the end of the displacement phase for better dynamic functions.

The large stiff pusher-plate in the man-made pump needs a cam-curve formation with a smooth start to close the inlet valve and avoid high pressure gradients. This is, by the heart, done by an initiating time that can be registered by ECG where the initiated muscle-forces are powering the AV-piston from its periphery towards the ring of annulus fibrosis. The atria contractions have by especially lifting the peripheral muscular part of the AV-piston towards the top, the base of the heart, made the outer contours of the ventricular muscles connections to annulus fibrosis in a cross-section view, especially on the right side, to look like a hook (see FIG. 8). Once the ventricular contractions start, there will be sliding motions of the AV-piston between the pericardial sack and its enclosed upper and lower blood-volumes. These motions will, by the first lever principle, create a geared down peripheral pumping effect until the whole DeltaV-piston with its valves and support of power as a whole unit can take part in the displacement work. This geared down work will create internal volume redistributions and close the inlet valves with a minimum of back-flows. It also prepares the heart-muscles as construction material and especially IVS to be ready to withstand increasing pressures. With reduced power and/or impaired ventricular contractions (dyssynchronies), the total stroke-length of the AV-piston will be reduced. The peripheral geared down motions needing less power, will still generate and displace direct DeltaV-volumes though the motions and displacement of the more flat part of the common AV-piston, the ring of annulus fibrosis in severe cases can be heavily reduced. In these cases the ventricular ejection phase will through a long tension-to-volume phase directly be transformed into the slow DeltaV-function phase. The lifting functions of the atria contractions can in these cases be life saving.

Investigations of the heart with old or new investigating methods bring a lot of information that may be very hard to interpret. Every mechanical device can be expressed in state diagrams if the mechanics behind the working principles are fully known. This has not been the case concerning the heart as a mechanical device. The filling and regulating functions of the heart has been debated during centuries. The complex architecture and motions of the heart together with unknown mechanics, makes it almost impossible to determine the contributions of different activities and functions within the heart even at very low flow and heart rates. At higher flow and heart rates, all investigating methods, more or less, show a chaotic output of information. This, together with the general belief that the heart is pumping with squeezing functions, are probably the reasons why activities of the heart muscle cells have been in focus in trying to understand and analyze the functions of the heart.

In view of the foregoing the inventor's have identified a great demand of fast, accurate and reliable ways of determining and presenting relevant information representing the true pumping procedure of the heart, such that correct diagnosis and therapy may be determined.

Thus, the object of the present invention is to achieve an improved graphical interface adapted to present relevant information such that correct diagnosis and therapy easily may be determined.

SUMMARY OF THE INVENTION

The above-mentioned object is achieved by the present invention according to the independent claim.

Preferred embodiments are set forth in the dependent claims.

According to the invention input values are applied to a state machine interface system, e.g. a dedicated software, adapted to identify, validate and divide the hearts mechanical boundary conditions as being a piston-pump or more precise a cluster state machine of DeltaV-pump state-machine and heart-muscle-cell state machines, into phases represented as e.g. state-diagrams. Finally, the state machine interface system presents the investigated values as e.g. trend-curve formations reflecting the major functions of the heart during the whole cycle in a compact way that is easy to understand and analyze. The interface system can also receive and generate values for simulations, evaluations, analyzing, and database handlings (see FIG. 9). Even when using sparse information presented as values or other events and used as input values in individual related state—diagrams and related databases, the concluded state diagrams and/or trend-curves may include relevant information such that the heart's condition correctly may be illustrated.

The object of the present invention is achieved by identifying the phases of the heart-cycle, evaluate their correct time-intervals by local state-diagrams registered from one or more sites, or registration points, by one or more registration methods and then statistically find the most representative global state-diagram. Once that is found other information related to the heart's functions may be added to the phases of the global state-diagram like the ECG registration, validated local and global stroke-length of the piston, local and global thickening and motions of the heart-muscle generating state-diagram oriented ejection fractions, impedance-curves registered by pacemakers, central and peripheral flow and blood-pressures including the cardiac perfusion, velocity- and tension changes inside and outside the heart its vessels and other internal and external produced values, chemical and electrical stimulation that are related to the heart and its circulatory functions.

SHORT DESCRIPTION OF THE APPENDED DRAWINGS

FIGS. 1*a*-1*f* schematically illustrate the different phases of a DeltaV-pump.

FIG. 2 illustrates a man-made flexible DeltaV-pump.

FIGS. 3*a*-3*d* illustrate examples of 3D-representations of a heart, achieved in accordance with the present invention.

Figure 16A:
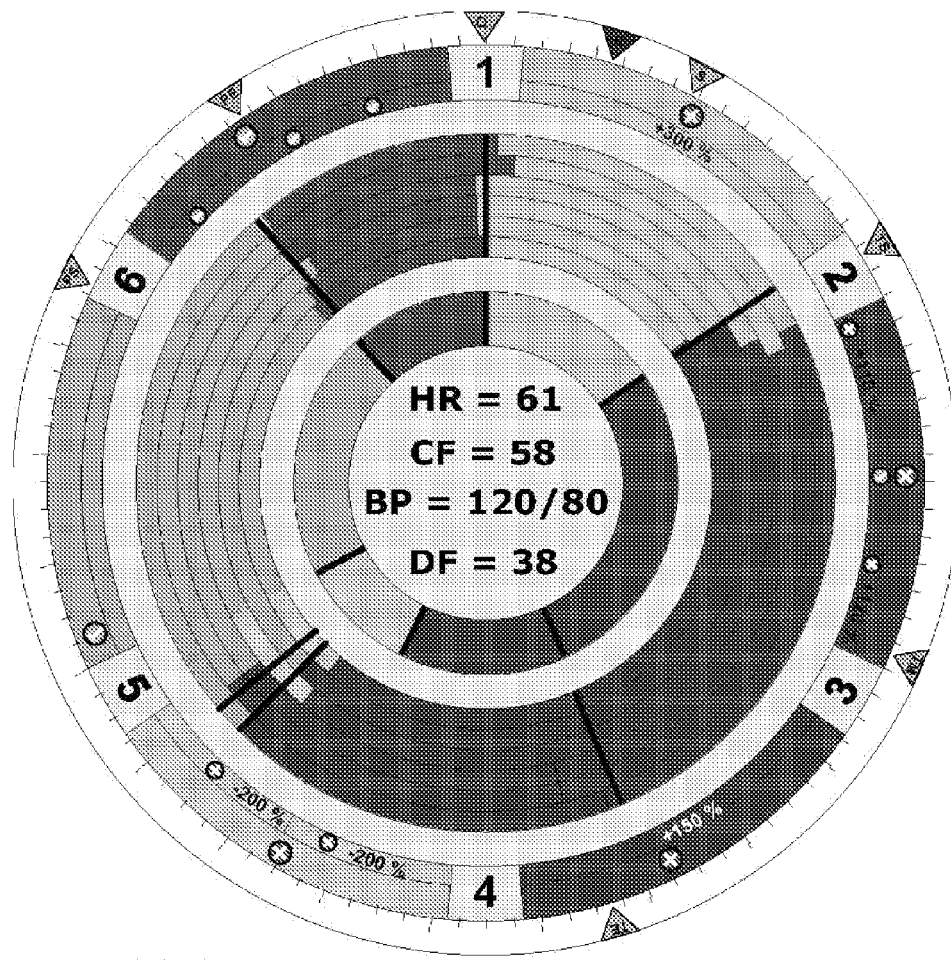
Figure 16B:
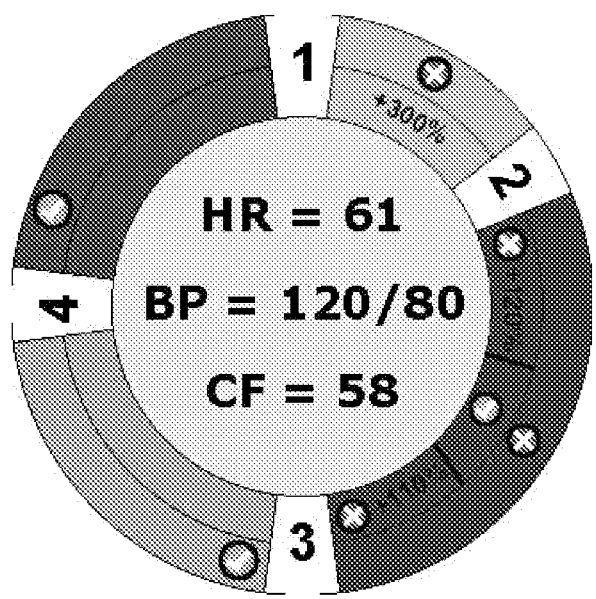

FIGS. 16a,b illustrate examples of graphic validations of global state-diagrams with sub-phases (FIG. 16a) and by peripheral pressure and or flow monitoring together with ECG registrations as simplified state-diagrams (FIG. 16b).

DETAILED DESCRIPTION OF PREFERRED EMBODIMENTS OF THE INVENTION

In accordance with the above description the heart's pump-cycle has been divided into six main phases:
1. Slow ΔV-Function
2. Atrial Contraction
3. Volume to Tension
4. Ventricular Ejection
5. Tension to Volume
6. Rapid ΔV-Function The six phases are the kernel in the dedicated software that in a first step is loaded by information from input means to find and evaluate these phases and present these as global individual related and validated state-diagrams, see FIG. 9.

This can be done by using input data from simple or more complex investigating methods or monitoring devices inside and/or outside the body, directly and/or indirectly associated to the heart's functions and also accept input values to produce simulations and corrections.

As a second step investigated values may be added into the states indicating when, where, how and why these values have the values they have.

In a third step further simulation, analyzing, validation and database units may be added.

The invention will be described by using TVI as an investigating and monitoring device.

Values registered as e.g. velocities may be used to roughly identify these phases.

Figure 10:
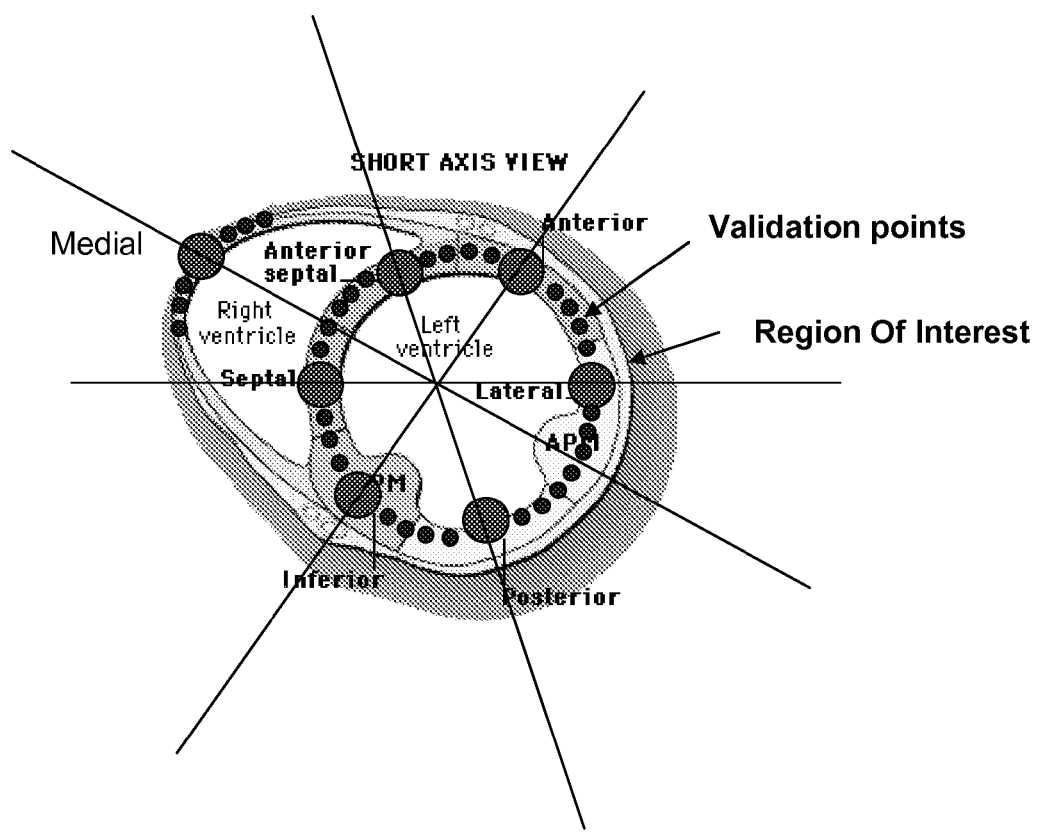
FIG. 10 illustrates measurement and validation points in a cross-sectional view of the heart used in connection with the present invention.

Exemplary positions for the 1 to n registration points positioned anywhere inside and/or outside the heart are illustrated in FIG. 10 and are indicated as small and large dots.

The exact onset and end of these phases are easier to detect as closer to the heart they are registered. The real true onset and end of these phases may even with the high resolution techniques as TVI, especially at disturbed muscular contractions, be hard to define because of complex motions and registration artifacts. Adding boundary conditions according to the defined states as described above, measuring more sites, with or without other complimentary investigating methods like ECG, the software will, like an image-processing technique, statistically find the most representative global state-diagram of the right and left ventricles.

Figure 2:
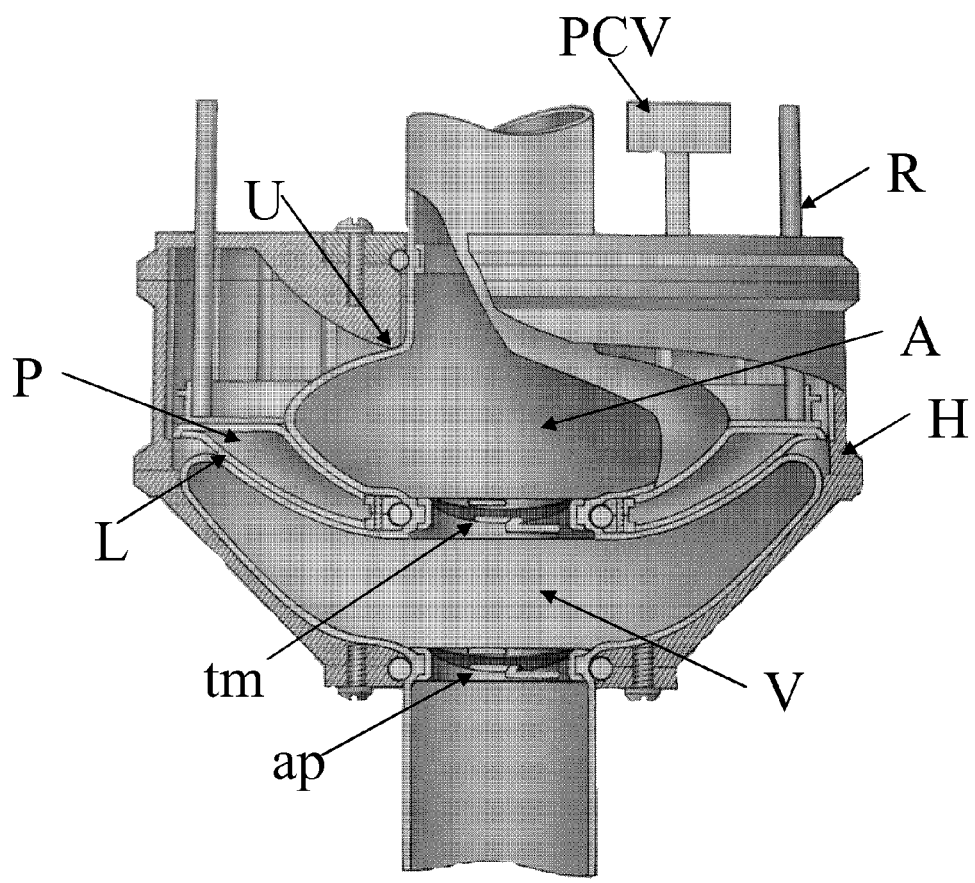
Figure 3A:
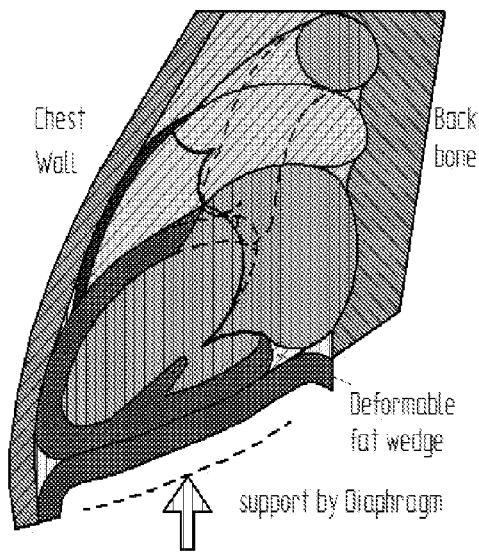
Figure 3B:
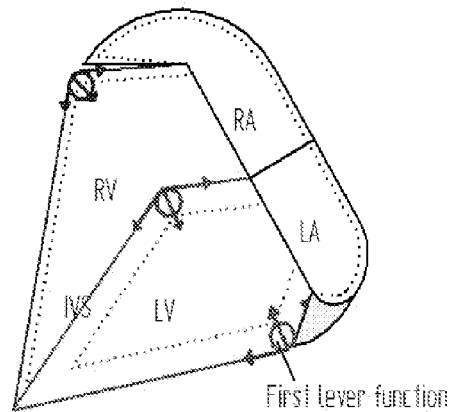
Figure 3C:
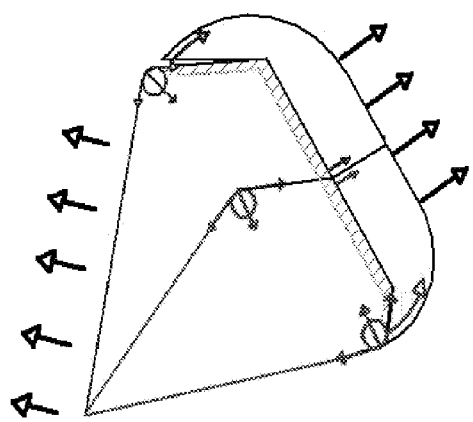
Figure 3D:
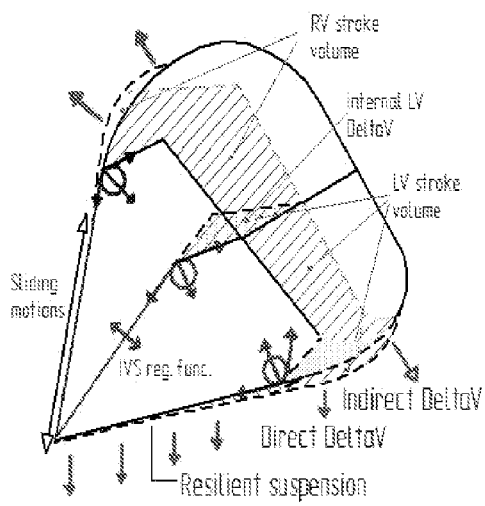
Figure 4:
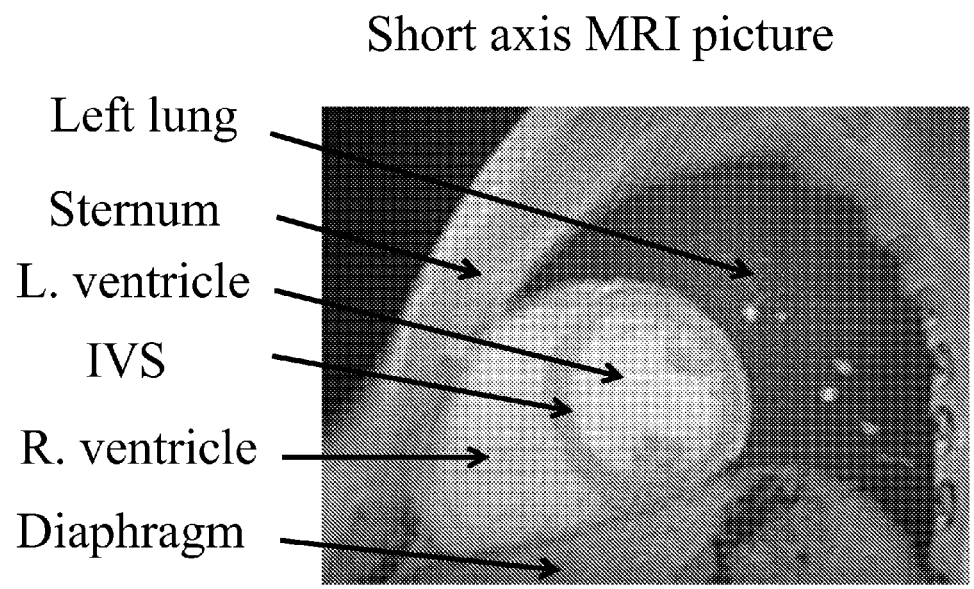
FIG. 4 is a magnetic resonance image (MRI) picture showing a short axis view of the heart and surrounding tissue.
Figure 5:
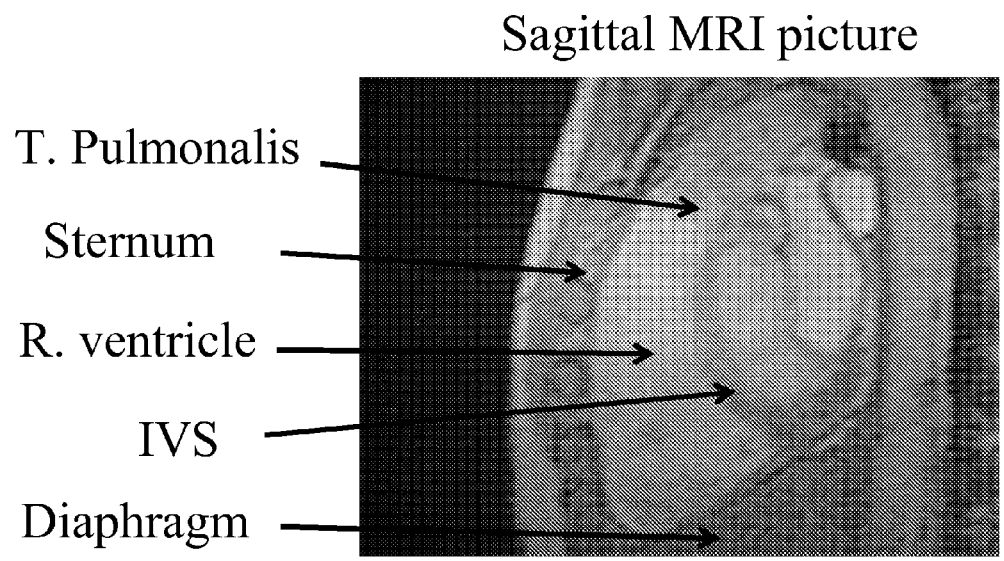
FIG. 5 is an MRI picture showing a sagittal view of the heart and surrounding tissue.
Figure 6:
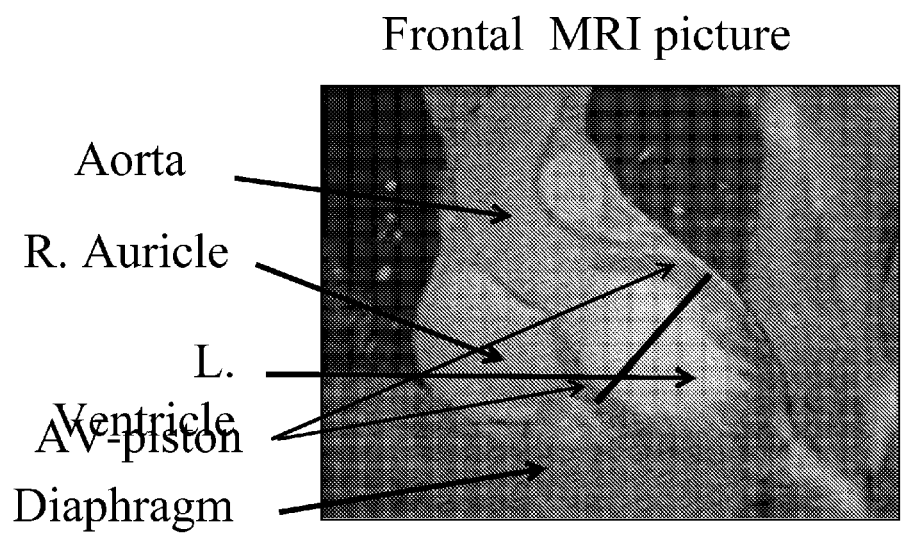
FIG. 6 is an MRI picture showing a frontal view of the heart and surrounding tissue.
Figure 7:
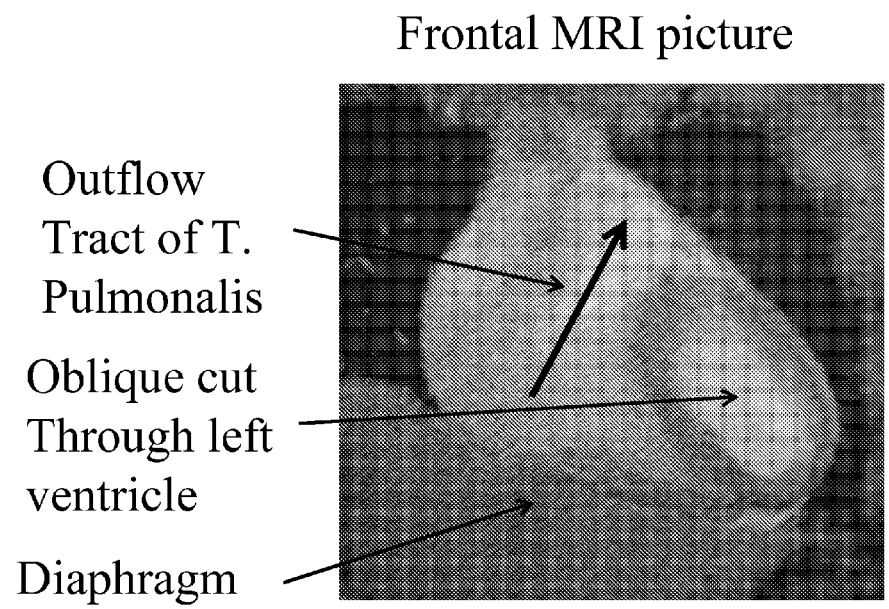
FIG. 7 is another MRI picture showing a frontal view of the heart and surrounding tissue.
Figure 8:
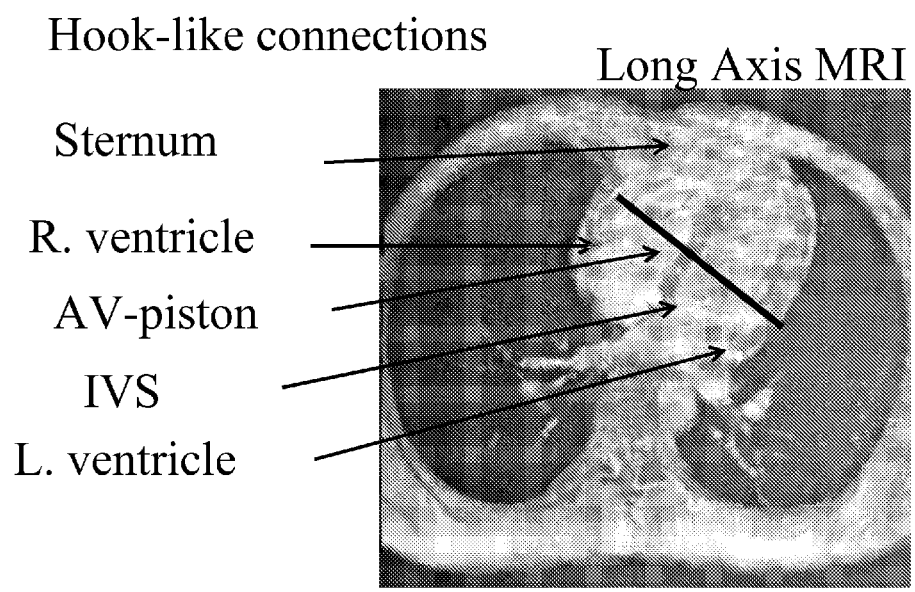
FIG. 8 is an MRI picture showing a long axis view of the heart and surrounding tissue.
Figure 9:
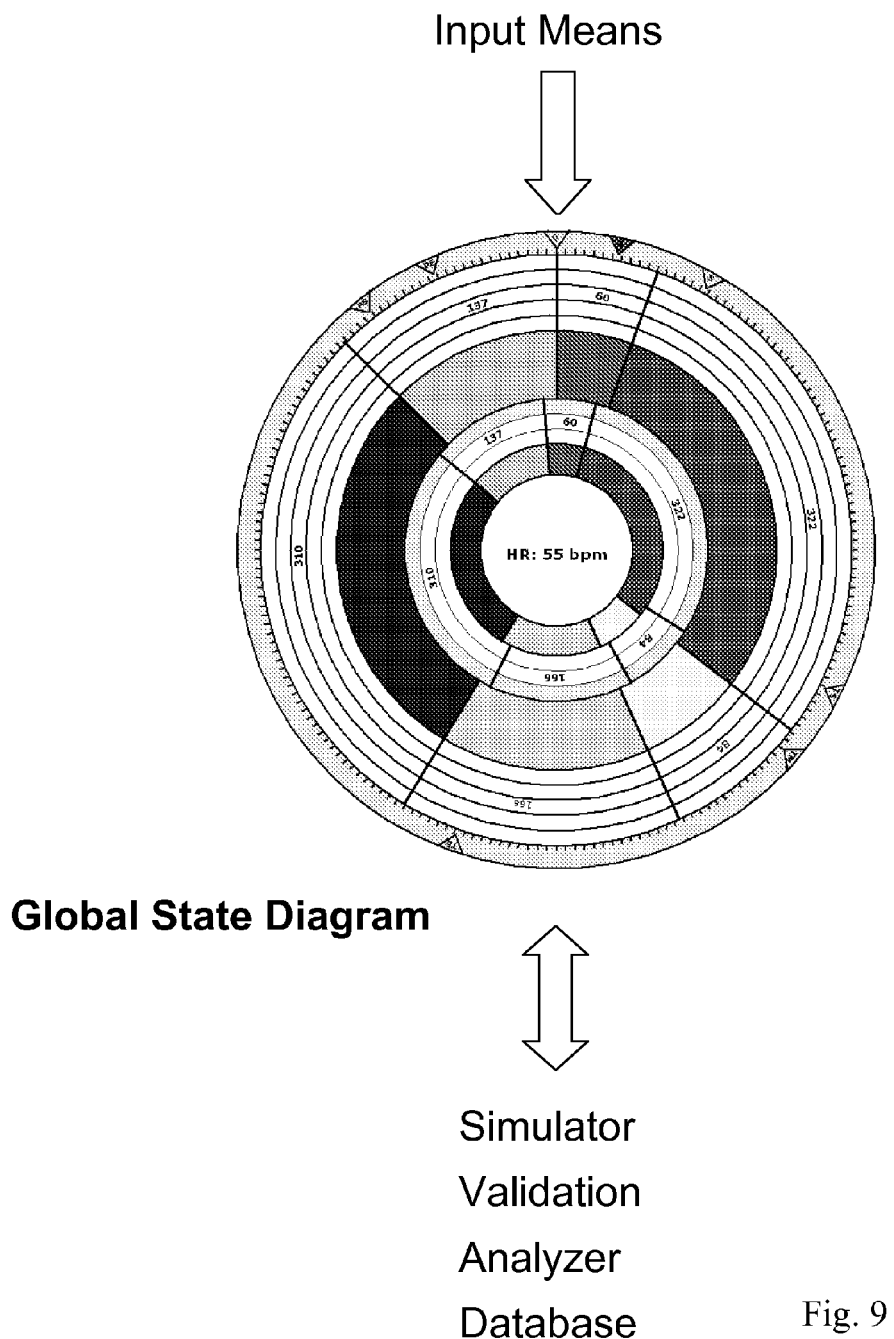
FIG. 9 illustrates a global state diagram generated in accordance with the present invention.

The phases are presented as an internal respectively external colour-coded circle showing the time-duration in milliseconds of different phases during a heart-cycle, see FIG. 9.

Figure 11:
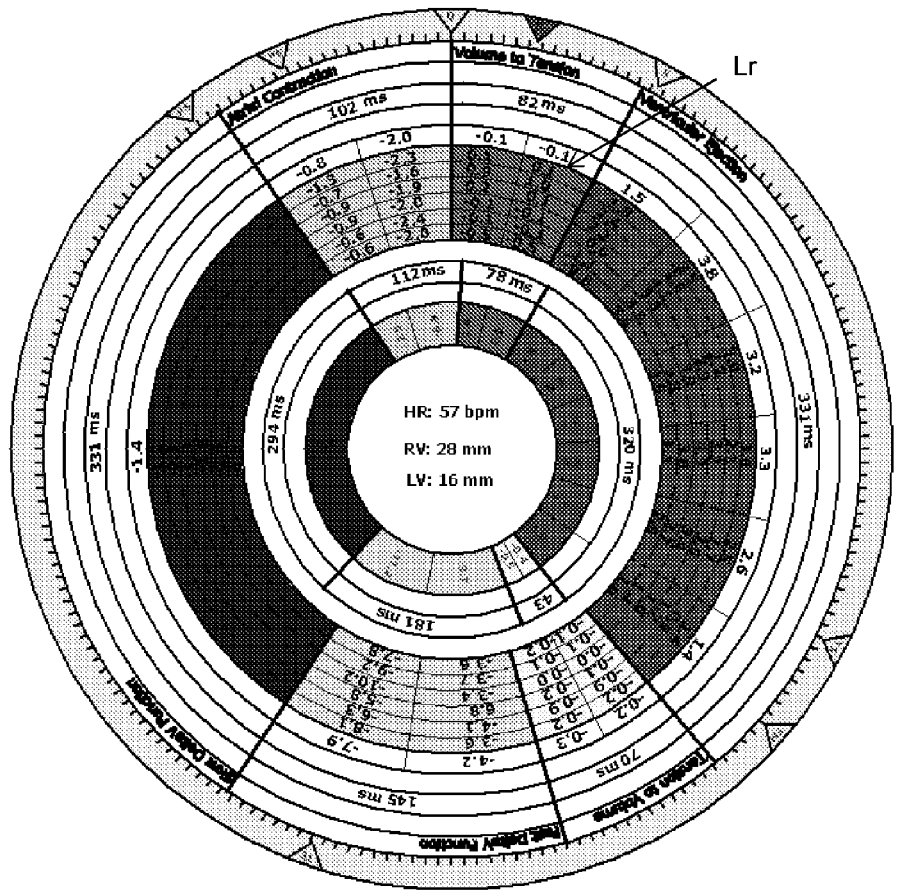
FIG. 11 illustrates a global state diagram generated in accordance with the present invention that in particular displays the relevant stroke-lengths.
Figure 12:
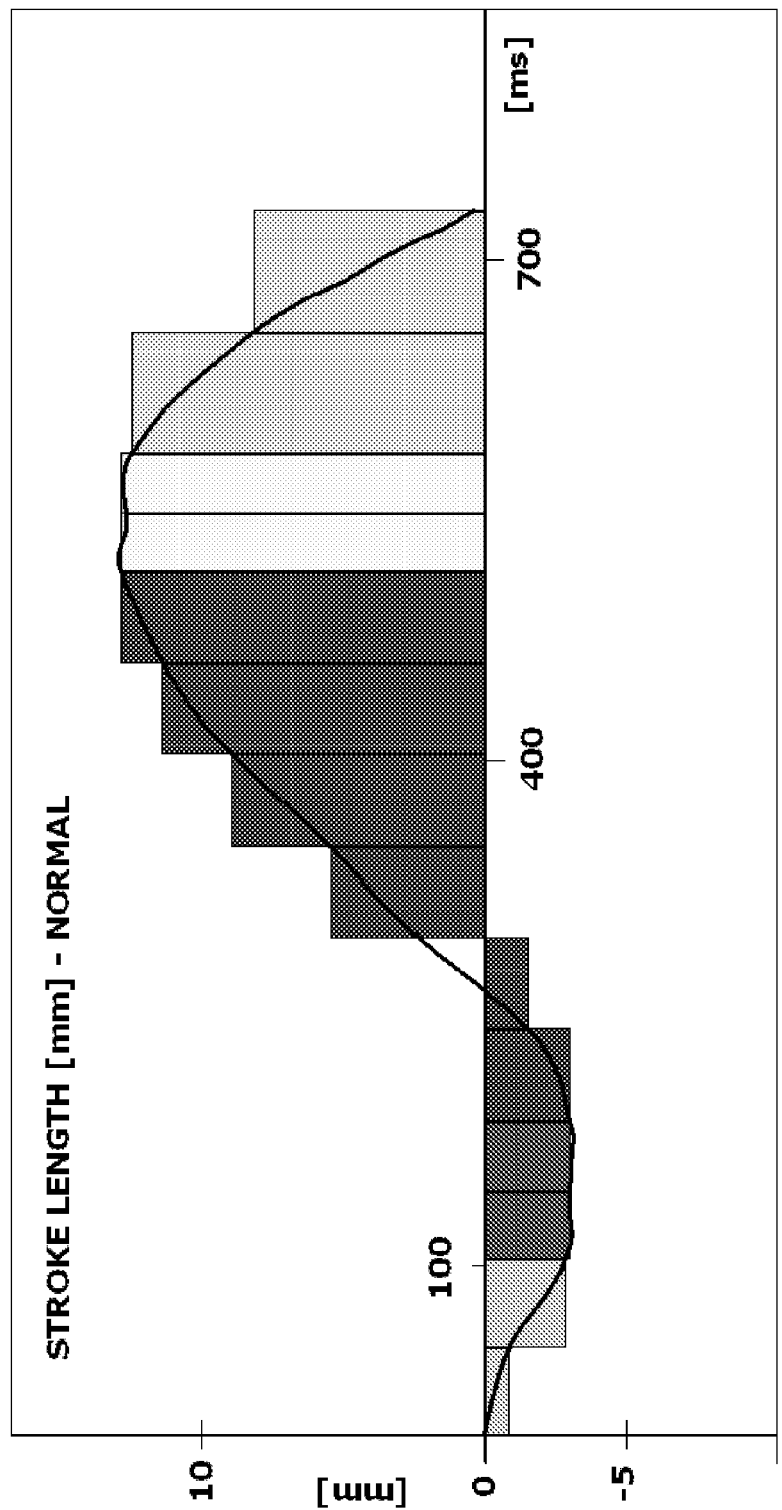
FIG. 12 illustrates a stroke-length curve of a normal subject.

Once that is done different kinds of other functions may be added to the global state-diagram which is illustrated in FIG. 11. In FIG. 11 is shown the results of AV-piston motions at seven sites (large dots) close to the ring of annulus fibrosis in positions illustrated in FIG. 10. The motions of these points are also statistically validated by measuring adjacent points that as good as possible represent the piston motions at these sites. The seven sites are represented by seven colour coded rings according to the global state-diagram shown in FIG. 11. The most central ring represents the "medial" point and the motions of the common AV-piston done by the right ventricular muscle. The main phases are divided into sub-phases by radial short lines (Ls) in order to visualize local changes (represented as values displayed within the sectors of the rings) and global changes (represented as values displayed as summarized values of each sector) of the AV-piston motions. The global values will finally serve as values in trend-curve algorithms that very clearly illustrate the heart's performances through its phases. This is illustrated in FIG. 12.

As illustrated by the exemplary state diagram in FIG. 11, the activities are represented by graphical illustrations, where one represents the state diagram from the left half of the heart, another represents a state diagram from the right half of the heart and/or a third represents a state diagram of the activities of ventricular septum. Each presented heart cycle phase, and/or sub-part of heart cycle phase, has been assigned related values from the input signals and/or other related signals. As discussed above and based upon a state diagram as illustrated in FIG. 11 at least one trend-curve is created being a representation of the assigned values from one to all heart cycle phases, or from one or many sub-parts of one heart cycle phase.

According to one embodiment a trend-curve is created being a representation of the mean value of the assigned values from one to all heart cycle phases, or from one or many sub-parts of one heart cycle phase. This is illustrated in FIGS. 11 and 12. As an example, during the second sub-part of the ventricular ejection phase the mean value has been determined to 3,8 being the mean value of the different measurement values 3,5 3,8 4,1 3,8 3,9 and 3,6. The trend-curve illustrated in FIG. 12 may then be determined by using the calculated mean values.

In fact the trend curves may be generated by any investigated parameter that is linked to the mechanical functions of the heart and that may be seen as cam-curve profiles that are reflecting the motions of the AV-piston during the heart's different phases.

Figure 13:
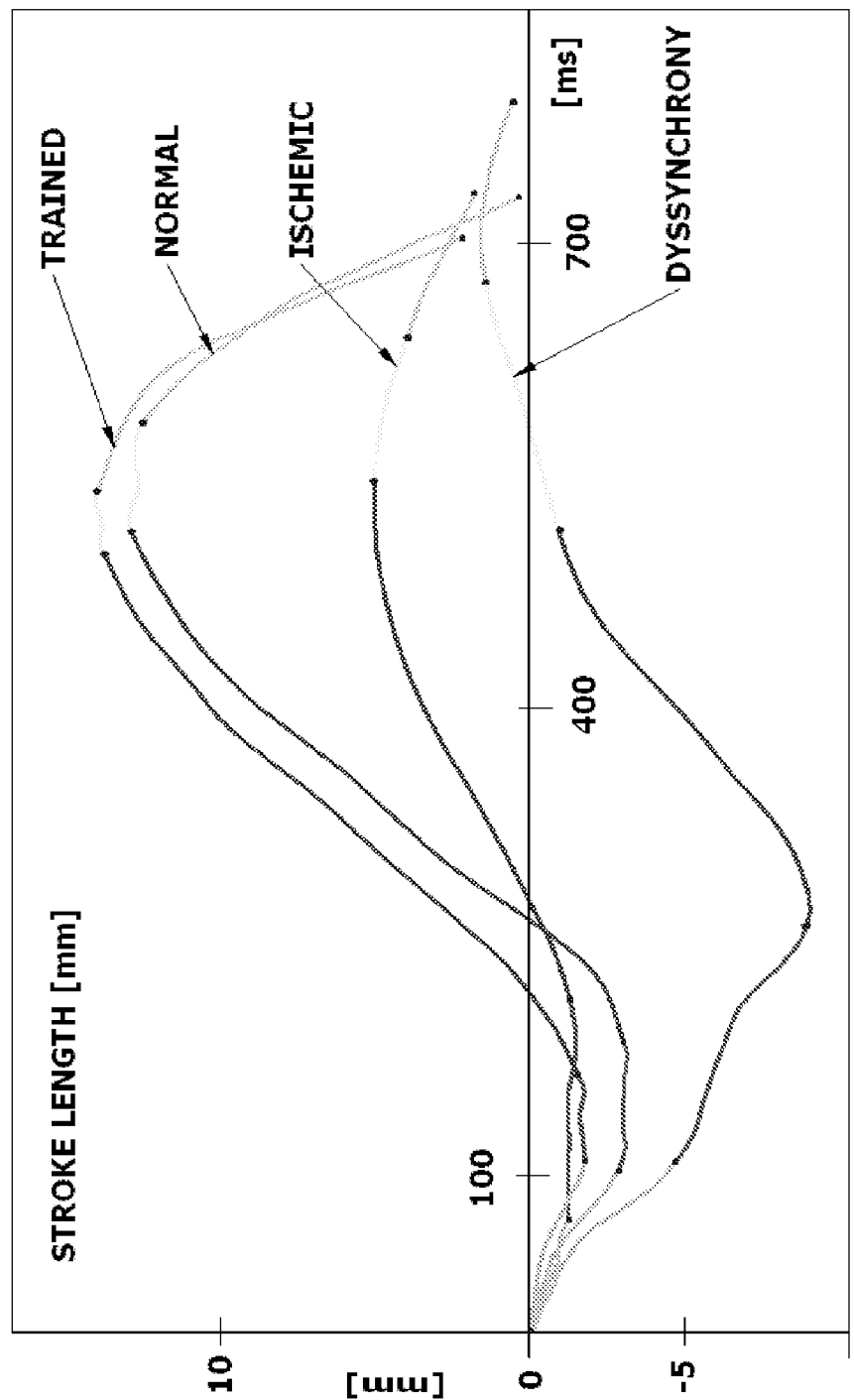
FIG. 13 illustrates stroke-length curves of a normal, an ischemic, and a trained subject and a subject suffering from dyssynchrony.

FIG. 13 shows four trend-curves representing the trend-curves of a TRAINED, a NORMAL, an ISCHEMIC and a DYSSYNCRONIC subject. The zero-line is equal to the neutral position of the AV-piston. Negative values indicate that other forces then the direct DeltaV-function forces are working to increase the stroke-length of the AV-piston. These forces are generated by the atria contractions and as in dyssynchronic subjects by impaired muscular contractions that cannot resist the initial pressure gradients over the inlet valves. This division of the atria contribution contra the direct DeltaV-function contribution can only be seen in this type of investigation, but its effects may easily be seen by time-duration changes in the global state-diagram.

As clearly has been illustrated above, radical changes are easily detectable from the trend-curves and its related global state-diagrams that make them very suitable to be examined by software and databases.

Figure 14:
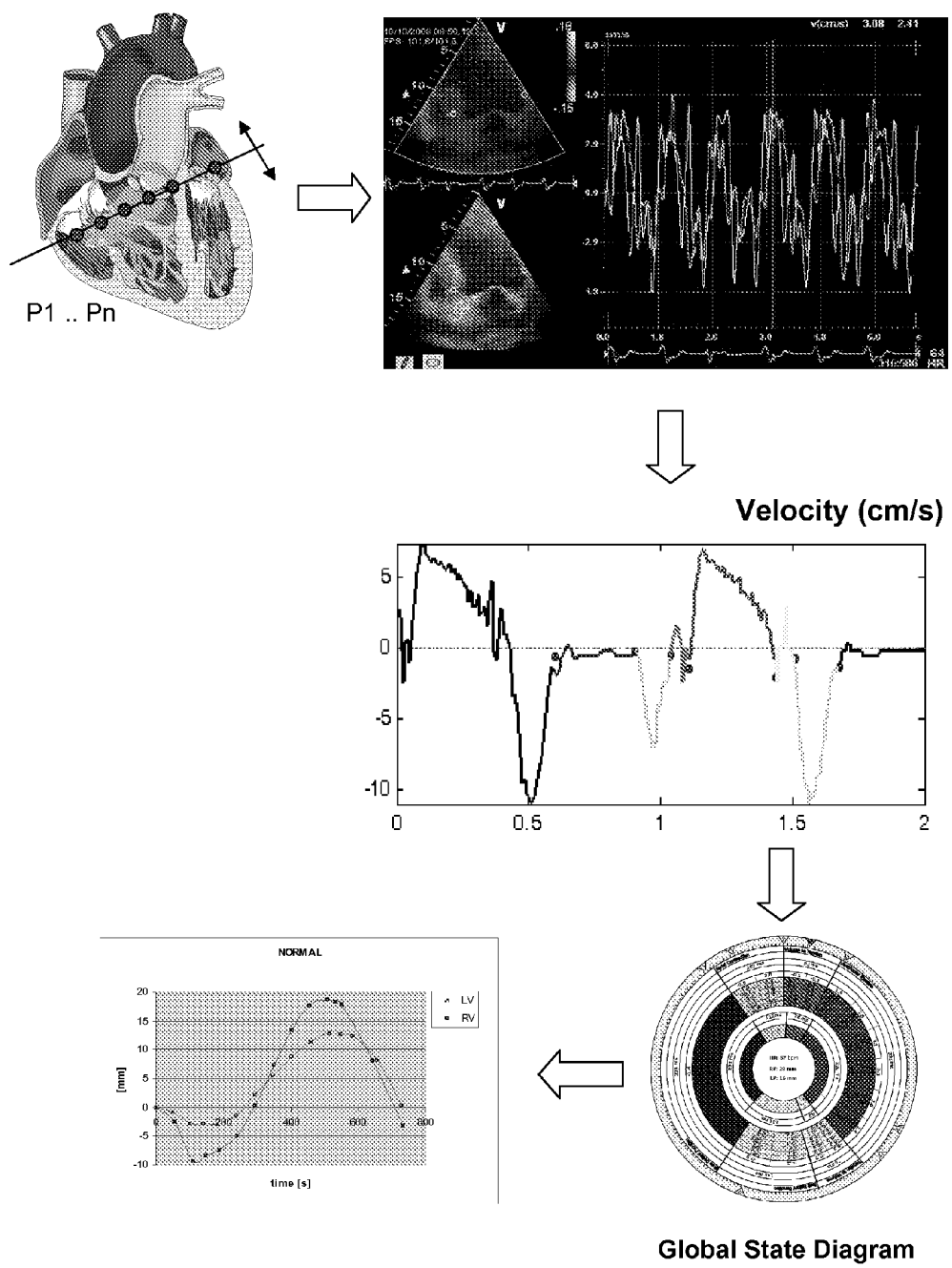
FIG. 14 is a schematic overview illustrating different aspects of the present invention.

FIG. 14 is an overview that stepwise illustrates what has been described above.

Preferably, the established values are communicated, e.g. via Internet or via the ordinary cell phone net, to a database that includes stored values representing different individual and/or global related values. The values are compared to the stored values and a status signal or report may be generated in dependence of the comparison. The status signal or report may then be used e.g. to determine and communicate correct medical therapy, to determine and communicate the correct medical diagnosis, and/or to improve a training program for an athlete.

Figure 15:
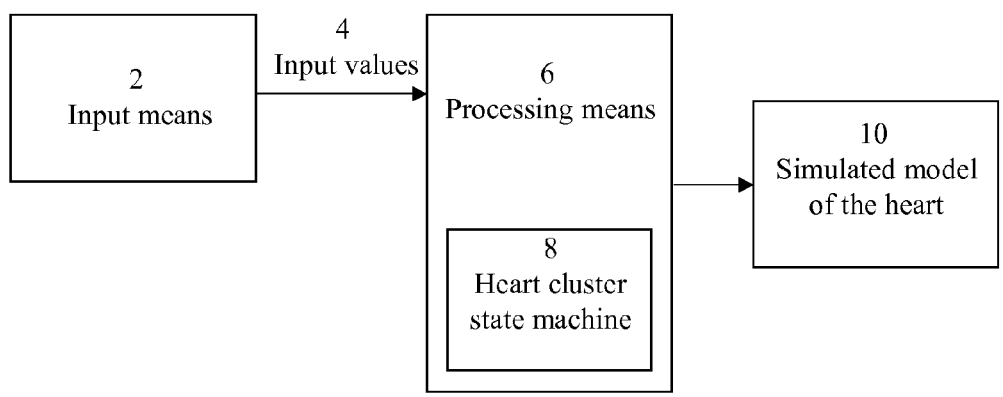
FIG. 15 is a block diagram illustrating the main parts of the state machine interface system according to the present invention.

With references to FIG. 15 the present invention is realised by a heart state machine analyzer and/or simulator that includes a state machine interface system. The interface system further includes an input means 2 for receiving signals being transformed to time related trigging points 4, and for applying the trigging points to a processing means 6 that is adapted to determine, by using the heart state machine analyzer algorithms, a relational database system, enabling graphical representations in two or three dimensions, to be stored in a storing means, being such that it both satisfies the working regimen of the heart muscle cell state machine and the working regimen of the ΔV-pump state machine of the heart cluster state machine. The processing means is adapted to communicate information using the database system in order to determine a therapeutic treatment, e.g. training, surgery or pharmaceutical treatments.

The input means may receive single or mixed imaging and other data of the heart obtained by ultrasound, magnetic resonance, x-ray, gamma radiation or other data of the heart and physiological activities measured by pulse plethysmography, pulse and/or flow measurements, pressure and/or volume changes over time in order to improve and validate data.

FIGS. 16a,b (observe new names and color codes compared to previous diagrams) illustrate examples of graphic validations of global state-diagrams with sub-phases, as generated by TWI for doctors' use (FIG. 16a) and by peripheral pressure and or flow monitoring together with ECG registrations as simplified state-diagrams for individuals' use (FIG. 16b).

Below respective FIGS. 16a and 16b are indicated the color codes used in the figures with explaining text.

The following abbreviations are used in the figures:
HR=Heart Rate
DF=Dynamic Factor
CF=Coronary blood Flow
BP=Blood Pressure Encircled symbol "√" in the segments presents in percentage the measured value inside the normal distribution.

Encircled symbol "x" in the segments presents in percentage the measured value outside the normal distribution.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A state machine interface system, comprising:
a processor, and
state machine algorithms, and
a graphical user interface adapted to receive signals from at least one sensor device that are related to physiological activities of the heart and/or a circulatory system of a living being, wherein:
said state machine algorithms are adapted to determine phases of heart cycles based upon said signals,
said different phases of the heart cycle are determined by said state machine algorithms in a heart cluster state machine simulating the heart, and optionally the circulatory system, achieved by fusions of finite heart muscle cell state machines to form a ΔV-pump state machine, and
said determined heart cycle phases are evaluated by determining their respective local state diagram based upon said signals such that the respective correct time duration is determined for each heart cycle phase, and then determining the most representative global state diagram, said determined local and global state diagrams are presented at the graphical user interface such that the temporal relations between the different phases are illustrated.

2. The state machine interface system according to claim 1, wherein the heart cycle phases are graphically presented as one or several graphical illustrations, e.g. overlapping circle diagrams, rings or bars, presenting different activities of the heart and circulatory system at one to several locations, arranged as state diagrams, where the phases are represented as time segments with lengths depending on the duration of the respective phase.

3. The state machine interface system according to claim 2, wherein activities are represented by graphical illustrations, one represents the state diagram from the left half of the heart, another represents a state diagram from the right half of the heart and/or a third represents a state diagram of the activities of ventricular septum.

4. The state machine interface system according to claim 3, wherein each presented heart cycle phase, and/or sub-part of heart cycle phase, has been assigned related values from said input signals and/or other related signals.

5. The state machine interface system according to claim 3, wherein each presented heart cycle phase have a predetermined colour, and/or pattern, coding and/or percentage scoring in order to clearly distinguish and quantify the phases from each other.

6. The state machine interface system according to claim 2, wherein each presented heart cycle phase, and/or sub-part of heart cycle phase, has been assigned related values from said input signals and/or other related signals.

7. The state machine interface system according to claim 2, wherein each presented heart cycle phase have a predetermined colour, and/or pattern, coding and/or percentage scoring in order to clearly distinguish and quantify the phases from each other.

8. The state machine interface system according to claim 2, wherein the displayed information is continuously updated in real-time.

9. The state machine interface system according to claim 1, wherein each presented heart cycle phase, and/or sub-part of heart cycle phase, has been assigned related values from said input signals and/or other related signals.

10. The state machine interface system according to claim 9, wherein at least one trend-curve is created being a representation of said assigned values from one to all heart cycle phases, or from one or many sub-parts of one heart cycle phase.

11. The state machine interface system according to claim 10, wherein said trend-curve is graphically presented such that a zero-line is equal to the neutral position of the AV-piston, and that negative values indicate that other forces than the direct DeltaV-function forces are working to increase the stroke-length of the AV-piston.

12. The state machine interface system according to claim 11, wherein each presented heart cycle phase have a predetermined colour, and/or pattern, coding and/or percentage scoring in order to clearly distinguish and quantify the phases from each other.

13. The state machine interface system according to claim 10, wherein each presented heart cycle phase have a predetermined colour, and/or pattern, coding and/or percentage scoring in order to clearly distinguish and quantify the phases from each other.

14. The state machine interface system according to claim 9, wherein at least one trend-curve is created being a representation of the mean value of said assigned values from one to all heart cycle phases, or from one or many sub-parts of one heart cycle phase.

15. The state machine interface system according to claim 14, wherein said trend-curve is graphically presented such that a zero-line is equal to the neutral position of the AV-piston, and that negative values indicate that other forces than the direct DeltaV-function forces are working to increase the stroke-length of the AV-piston.

16. The state machine interface system according to claim 9, wherein each presented heart cycle phase have a predetermined colour, and/or pattern, coding and/or percentage scoring in order to clearly distinguish and quantify the phases from each other.

17. The state machine interface system according to claim 14, wherein each presented heart cycle phase have a predetermined colour, and/or pattern, coding and/or percentage scoring in order to clearly distinguish and quantify the phases from each other.

18. The state machine interface system according to claim 1, wherein each presented heart cycle phase have a predetermined colour, and/or pattern, coding and/or percentage scoring in order to clearly distinguish and quantify the phases from each other.

19. The state machine interface system according to claim 1, wherein the displayed information is continuously updated in real-time.

20. The state machine interface system according to claim 1, wherein said established values are communicated to a database that includes stored values representing individual and/or global related values, said established values are compared to said stored values and a status signal or report is generated in dependence of said comparison, wherein said status signal or report is used e.g. to determine and communicate correct medical therapy, to determine and communicate the correct medical diagnosis, and/or to improve a training program for an athlete.

* * * * *